United States Patent [19]
Tran

[11] Patent Number: 5,744,469
[45] Date of Patent: Apr. 28, 1998

[54] METHOD FOR TREATING DERMATITIS

[75] Inventor: Pierre V. Tran, Carmel, Ind.

[73] Assignee: Eli Lilly and Company, Indianapolis, Ind.

[21] Appl. No.: 756,996

[22] Filed: Nov. 26, 1996

[51] Int. Cl.$^6$ .......................... A61K 31/55; A61K 31/38
[52] U.S. Cl. .......................... 514/220; 514/249; 514/438; 514/443; 514/858; 514/859; 514/860; 514/861; 514/862; 514/863; 514/864; 514/865
[58] Field of Search .......................... 514/220, 249, 514/438, 443, 858, 859, 860, 861, 862, 863, 864, 865

[56] References Cited

U.S. PATENT DOCUMENTS 5,229,382  7/1993  Chakrabarti et al. .................. 514/220

*Primary Examiner*—Kevin E. Weddington
*Attorney, Agent, or Firm*—Arleen Palmberg; MaCharri Vorndran-Jones; David E. Boone

[57]  ABSTRACT

The invention provides a method for treating fungal dermatitis comprising administering an effective amount of 2-Methyl-4-(4-methyl-1-piperazinyl)-10H-thieno[2,3-b][1,5]benzodiazepine to a patient in need thereof.

12 Claims, No Drawings

METHOD FOR TREATING DERMATITIS

FIELD OF THE INVENTION

This invention relates to a method for treating fungal dermatitis using 2-methyl-4-(4-methyl-1-piperazinyl)-10H-thieno[2,3-b][1,5]benzodiazepine.

BACKGROUND OF THE INVENTION

Fungal dermatitis is a troublesome condition which may produce mild inflammation; wherein the organism producing the dermatitis may persist indefinitely, causing intermittent remissions and exacerbations of a gradually extending lesion with a scaling, slightly raised border. Often the condition results in a sudden visicular and bullous disease of the feet or an inflamed boggy lesion of the scalp.

It is known that fungal dermatitis may be caused by a variety of organisms. Most preferably, 2-Methyl-4-(4-methyl-1-piperazinyl)-10H-thieno[2,3-b][1,5]benzodiazepine is used for the treatment of a condition selected from the group consisting of *Tinea corporis*, *Tinea pedis*, *Tinea unguium*, *Tinea capiris*, *Tinea cruris*, and *Tinea barbae*. It is preferred that the condition is selected from *Tinea corporeis* and *Tinea pedis*. Most such infections respond to topical antifungal preparations such as the imidazoles. Certain cases may be resistant to such treatment and require systemic treatment using agents such as Griseofulvin; however, this agent is frequently associated with headaches, gastrointestinal distress, photosensitivity, rashes, or leukopenia. Angioedema has been reported, vertigo, and sometimes transient hearing reduction. Ketoconazole is an oral imidazole derivative which may be used for systemic treatment; however, this compound is associated with liver toxicity and other serious side effects. Therefore, effective agents having a favorable side effect profile are desired. Surprisingly, Applicant has discovered that 2-methyl-4-(4-methyl-1-piperazinyl)-10H-thieno[2,3-b][1,5]benzodiazepine can be useful for treating fungal dermatitis.

The 2-methyl-4-(4-methyl-1-piperazinyl)-10H-thieno[2,3-b][1,5]benzodiazepine compound is described in U.S. Pat. No. 5,229,382 ('382), herein incorporated by reference in its entirety.

Fungal dermatitis can be particular troublesome to treat in non-compliant patients such as those suffering from psychotic conditions. The 2-methyl-4-(4-methyl-1-piperazinyl)-10H-thieno[2,3-b][1,5]benzodiazepine compound can be particularly useful for treating fungal dermatitis in psychotic patients as the 2-methyl-4-(4-methyl-1-piperazinyl)-10H-thieno[2,3-b][1,5]benzodiazepine compound can be administered as part of the patients' usual treatment regimen.

SUMMARY OF THE INVENTION

The presently claimed invention provides a method for treating fungal dermatitis comprising administering an effective amount of a 2-methyl-4-(4-methyl-1-piperazinyl)-10H-thieno[2,3-b][1,5]benzodiazepine compound to a patient in need thereof.

DETAILED DESCRIPTION OF THE INVENTION

2-Methyl-4-(4-methyl-1-piperazinyl)-10H-thieno[2,3-b][1,5]benzodiazepine, is a compound of Formula(I):

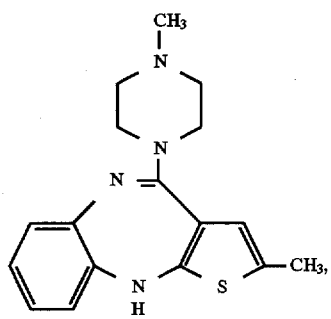

and is described in the '382 patent. The '382 patent teaches that 2-methyl-4-(4-methyl-1-piperazinyl)-10H-thieno[2,3-b][1,5]benzodiazepine can be useful for the treatment of psychotic conditions and mild anxiety states.

For example, 2-methyl-4-(4-methyl-1-piperazinyl)-10H-thieno[2,3-b][1,5]benzodiazepine has been assessed in a number of standard behavior tests predictive of antipsychotic activity. The claimed compound antagonized apomorphine-induced climbing behavior and hypothermia in mice. See Moore, N. A. et al *Psychopharmacology* 94 (2), 263–266 (1988). The compound also inhibits conditioned avoidance response in rats, and has been found to have a favorable profile of activity in a number of in vitro binding assays, designed to measure the degree of binding to neural receptors. For example, the compound is active at the dopamine D-1 and D-2 receptors as indicated by an IC50 of less than 1 uM in the 3H-SCH233390 (Billard, et al. *Life Sciences* 35:1885 (1984)) and the 3H spiperone (Seeman et al *Nature* 216:717 (1976)) binding assays respectively.

Further, 2-methyl-4-(4-methyl-1-piperazinyl)-10H-thieno[2,3-b][1,5]benzodiazepine is active at the 5-HT-2 receptor and 5-HT1C receptor. The in vitro results would indicate that the compound is effective in the treatment of psychotic conditions but less likely to induce extra pyramidal side-effects.

To Applicant's knowledge none of these mechanisms of action are thought to be associated with the treatment, prevention, or amelioration of fungal dermatitis.

Surprisingly, and in accordance with the present invention, Applicant has discovered that 2-methyl-4-(4-methyl-1-piperazinyl)-10H-thieno[2,3-b][1,5]benzodiazepine can be useful for treating or preventing fungal dermatitis.

As used herein the term "psychotic condition" shall refer to pathologic psychological conditions which are psychoses or may be associated with psychotic features. Such conditions include, but are not limited to the psychotic disorders which have been characterized in the DSM-III-R. *Diagnostic and Statistical Manual of Mental Disorders, Revised*, 3rd Ed. (1980). The DSM-III-R was prepared by the Task Force on Nomenclature and Statistics of the American Psychiatric Association, and provides clear descriptions of diagnostic categories. The skilled artisan will recognize that there are alternative nomenclatures, nosologies, and classification systems for pathologic psychological conditions and that these systems evolve with medical scientific progress.

The usefulness of 2-Methyl-4-(4-methyl-1-piperazinyl)-10H-thieno[2,3-b][1,5]benzodiazepine for treating fungal dermatitis can be demonstrated by clinical trial.

Such effectiveness for the treatment, amelioration of fungal dermatitis was shown in the following clinical trial:

The study was a double-blind, randomized, parallel, placebo and haloperidol-controlled study of 55 human subjects. The study was conducted in 23 study centers throughout the United States and Canada. Patients were randomized to one of the five treatment groups: placebo, 2-Methyl-4-(4-methyl-1-piperazinyl)-10H-thieno[2,3-b][1,5]benzodiazepine 5±2.5 mg/day, 2-Methyl -4-(4-methyl-1-piperazinyl)-10H-thieno[2,3-b][1,5]benzodiazepine 10±2.5 mg/day, 2-Methyl-4-(4-methyl-1-piperazinyl)-10H-thieno[2,3-b][1,5]benzodiazepine 15±2.5 mg/day, or haloperidol (15±5 mg/day). The acute phase lasted for 6 weeks with evaluations performed weekly followed by a double-blind extension phase of at least one year.

Fungal dermatitis occurred statistically significantly less frequently in the 2-Methyl-4-(4-methyl -1-piperazinyl)-10H-thieno[2,3-b][1,5]benzodiazepine 15±2.5 mg/day than in the haloperidol in the double-blind extension treatment phase.

2-Methyl-4-(4-methyl-1-piperazinyl)-10H-thieno[2,3-b][1,5]benzodiazepine is effective over a wide dosage range, the actual dose administered being dependent on the condition being treated. For example, in the treatment of adult humans, dosages of from about 5 to 20 mg per day may be used. A once a day dosage is normally sufficient, although divided doses may be administered. For treatment of fungal dermatitis in a human, a dose range of from about 2.5 to 17.5 mg, preferably 5 to 20 mg per day is suitable. It is particularly preferred to administer about 15 to about 20 mg/day of 2-Methyl-4-(4-methyl-1-piperazinyl)-10H-thieno[2,3-b][1,5]benzodiazepine for the treatment of fungal dermatitis in a human. Radiolabelled 2-Methyl-4-(4-methyl-1-piperazinyl)-10H-thieno[2,3-b][1,5]benzodiazepine, can be detected in the saliva and thus the compound can potentially be monitored in patients to assess compliance.

The 2-methyl-4-(4-methyl-1-piperazinyl)-10H-thieno[2,3-b][1,5]benzodiazepine compound will normally be administered orally for the treatment of fungal dermatitis, or may be administered by injection and, for this purpose, it is usually employed in the form of a pharmaceutical composition. Other suitable formulations are taught in the '382 patent. For the treatment of fungal dermatitis, a powder or transdermal formulation may be particularly desired.

As used herein, the term "mammal" shall refer to the Mammalia class of higher vertebrates. The term "mammal" includes, but is not limited to, a human. The term "treating" as used herein includes prophylaxis of the named condition or amelioration or elimination of the condition once it has been established.

For the treatment of fungal dermatitis, the patient may be a non-human mammal. In such instances, the 2-methyl-4-(4-methyl-1-piperazinyl)-10H-thieno[2,3-b][1,5]benzodiazepine compound may be administered as a feed additive, tablet, or transdermally.

Methods for preparing 2-methyl-4-(4-methyl-1-piperazinyl)-10H-thieno[2,3-b][1,5]benzodiazepine are provided by the '382 patent; however, the following examples may be instructive as well.

EXAMPLE 1

Technical Grade 2-methyl-4-(4-methyl-1-piperazinyl)-10H-thieno[2,3-b] [1,5]benzodiazepine

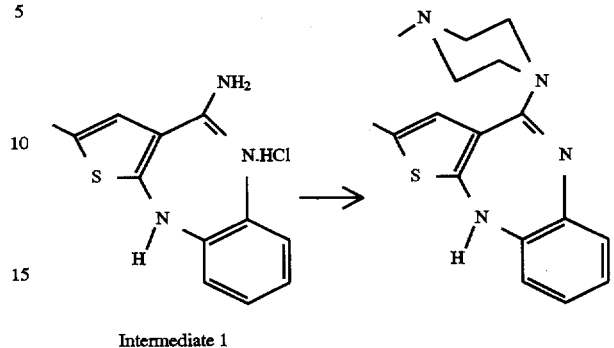

Intermediate 1

In a suitable three neck flask the following was added:
Dimethylsulfoxide (analytical): 6 volumes
Intermediate 1: 75 g
N-Methylpiperazine (reagent): 6 equivalents
Intermediate 1 can be prepared using methods known to the skilled artisan. For example, the preparation of the Intermediate 1 is taught in the '382 patent.

A sub-surface nitrogen sparge line was added to remove the ammonia formed during the reaction. The reaction was heated to 120° C. and maintained throughout the duration of the reaction. The reactions were followed by HPLC until ≦5% of the intermediate 1 was left unreacted. After the reaction was complete, the mixture was allowed to cool slowly to 20° C. (about 2 hours). Each reaction mixture was then transferred to an appropriate three neck round bottom flask and water bath. To this solution with agitation was added 10 volumes reagent grade methanol and the reaction was stirred at 20° C. for 30 minutes. Three volumes of water was added slowly over about 30 minutes. The reaction slurry was cooled to zero to 5° C. and stirred for 30 minutes. The product was filtered and the wet cake was washed with chilled methanol. The wet cake was dried in vacuo at 45° C. overnight. The product was identified as technical 2-methyl-4-(4-methyl-1-piperazinyl)-10H-thieno[2,3-b][1,5]benzodiazepine..
Yield: 76.7%; Potency: 98.1%
The procedure of Example 1 was repeated substantially as described above and provided a yield of 81% with a potency of 101.1%.

EXAMPLE 2

Technical Grade 2-methyl-4-(4-methyl-1-piperazinyl)-10H-thieno[2,3-b][1,5]benzodiazepine Intermediate 1 (supra) was suspended in DMSO (3.2 vol.) and toluene (4.5 vol.). A portion (≈0.65 vol.) of the solvent was removed by distillation at 120°-125° C. The mixture was cooled to 110° C., N-methylpiperazine(NHP, 4.2 equiv.) was added and the mixture heated back to reflux (120°-125° C.). Another portion (≈1 vol.) of the solvent was removed by distillation to dry the reaction mixture. A vigorous reflux was desired to drive the reaction to completion (about 7 hrs.) by removing ammonia from the reaction. The product was isolated by the slow addition of water (12.75 vol.) to the cooled (10° C.) reaction solution. The product was collected by filtration and washed with chilled water (2 vol.). The crude 2-methyl-4-(4-methyl-1-piperazinyl)-10H-thieno[2,3- b][1,5]benzodiazepine was dried in vacuo at 60° C. The product was recrystallized from hot toluene (5 vol.) to give a technical grade 2-methyl-4-(4-methyl-1-piperazinyl)-10H-thieno[2,3-b][1,5]benzodiazepine. After drying in vacuo at 50° C., the technical grade 2-methyl-4-(4-methyl-1-piperazinyl)-10H-thieno [2,3-b][1,5]benzodiazepine was recrystallized again from ethyl acetate (10 vol.)/toluene (0.62 vol.)/methanol (3.1 vol.) to give 2-methyl-4-(4-methyl-1-piperazinyl)-10H-thieno[2,3-b][1,5]benzodiazepine as a methanol solvate. The methanol solvate upon drying at >50° C. was converted to an anhydrous technical grade 2-methyl-4-(4-methyl-1-piperazinyl)-10H-thieno[2,3-b][1,5]benzodiazepine.

EXAMPLE 3

Tablet Formulation

A portion of the hydroxypropyl cellulose was dissolved in purified water to form a solution for granulation. The remaining hydroxypropyl cellulose (total of 4.0% w/w final tablet weight), which was an extra fine grade, was combined with the 2-methyl-4-(4-methyl-1-piperazinyl)-10H-thieno [2,3-b][1,5]benzodiazepine compound (1.18% w/w), lactose (79.32% w/w) and a portion of the crospovidone (5% w/w) in a high shear granulator. All ingredients were security sieved prior to addition and dry blended in the granulator. This mixture was then granulated with the hydroxypropyl cellulose solution in the high shear granulator. The granulation was wet sized using standard methods. The wet granulation was then dried in a fluidized bed dryer and sized. The material was then added to a tumble bin mixer.

The outside powders consisting of microcrystalline cellulose (granular) (10% w/w), magnesium stearate (0.5% w/w), and the remainder of the crospovidone were added to the sized granulation. The mixture was blended and compressed with the appropriate tooling on tablet compression equipment.

Subcoating

Hydroxypropyl methylcellulose (1.5% w/w) was mixed with purified water to form a solution. Core tablets were divided into approximately equal sections and spray coated with the hydroxypropyl methylcellulose solution. The operation was performed in a perforated coating pan.

Coating of Core Tablets

Color Mixture White (hydroxypropyl methylcellulose, polyethylene glycol, polysorbate 80, and titanium dioxide) was mixed with purified water to form the coating suspension. Subcoated tablets were divided into approximately equal sections and spray coated with the coating suspension described above. The operation was performed in a perforated coating pan.

The coated tablets were lightly dusted with carnauba wax and imprinted with appropriate identification.

We claim:

1. A method for treating fungal dermatitis comprising administering an effective amount of 2-methyl-4-(4-methyl-1-piperazinyl)-10H-thieno[2,3-b][1,5]benzodiazepine or a pharmaceutically acceptable salt thereof to a patient in need of such treatment.

2. A method of claim 1 wherein the effective amount is from about 5 to about 20 mg/day for a human patient.

3. A method of claim 2 wherein the effective amount is from about 15 mg/day to about 20 mg/day.

4. A method of claim 3 wherein the 2-methyl-4-(4-methyl-1-piperazinyl)-10H-thieno[2,3-b][1,5]benzodiazepine is administered as a tablet.

5. A method of claim 3 wherein the effective amount is administered using a transdermal formulation.

6. A method of claim 1 wherein the patient is a mammal.

7. A method of claim 6 wherein the 2-methyl-4-(4-methyl-1-piperazinyl)-10H-thieno[2,3-b][1,5]benzodiazepine is administered as a feed additive.

8. A method of claim 6 wherein the patient is a human.

9. A method of claim 8 wherein the patient is not diagnosed with a psychotic condition.

10. A method of claim 1 wherein the patient suffers from fungal dermatitis.

11. A method of claim 10 wherein the fungal dermatitis is selected from the group consisting of *Tinea corporis*, *Tinea pedis*, *Tinea unguium*, *Tinea capitis*, *Tinea cruris*, and *Tinea barbae*.

12. A method of claim 11 wherein the fungal dermatitis is selected from the group consisting of *Tinea corporis* and *Tinea pedis*.

* * * * *